(12) United States Patent
Demetriou et al.

(10) Patent No.: US 6,485,959 B1
(45) Date of Patent: *Nov. 26, 2002

(54) CELL PRECONDITIONING AND CRYOPRESEVATION MEDIUM

(75) Inventors: Achilles A. Demetriou, Bel Aire, CA (US); Andreas Kamlot, Los Angeles, CA (US); Jacek Rozga, West Lake Village, CA (US)

(73) Assignee: Cedars Sinai Medical Center, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/168,349

(22) Filed: Oct. 7, 1998

(51) Int. Cl.$^7$ .............................. A61K 9/14; C12N 1/00; C12N 1/12; C12N 5/00; C12N 5/02
(52) U.S. Cl. .................... 435/243; 435/243; 435/252.1; 435/260
(58) Field of Search .................. 424/484, 488; 435/325, 243, 248, 260

(56) References Cited

U.S. PATENT DOCUMENTS

| | | | |
|---|---|---|---|
| 4,004,975 A | 1/1977 | Lionetti et al. | |
| 4,559,298 A | 12/1985 | Fahy | |
| 4,890,457 A | 1/1990 | McNally et al. | |
| 4,920,044 A | 4/1990 | Bretan | |
| 4,965,185 A | 10/1990 | Grischenko et al. | |
| 4,980,277 A | 12/1990 | Junnila | |
| 5,171,660 A | 12/1992 | Carpenter et al. | |
| 5,328,821 A * | 7/1994 | Fisher et al. .................... | 435/1 |
| 5,336,616 A * | 8/1994 | Livesey et al. .......... | 435/240.2 |
| 5,358,844 A | 10/1994 | Stossel et al. | |
| 5,364,756 A | 11/1994 | Livesey et al. | |
| 5,378,601 A | 1/1995 | Gepner-Puszkin | |
| 5,424,207 A | 6/1995 | Carpenter et al. | |
| 5,504,002 A | 4/1996 | Aoyagi | |
| 5,552,267 A * | 9/1996 | Stern et al. .................... | 435/1.1 |
| 5,622,867 A * | 4/1997 | Livesey et al. ................ | 436/18 |
| 5,635,344 A | 6/1997 | Garcia et al. | |

FOREIGN PATENT DOCUMENTS

| | | |
|---|---|---|
| WO | WO 86/00812 | 2/1986 |
| WO | WO 97/43899 | 11/1997 |
| WO | PCT/US99/23342 | 3/2000 |

OTHER PUBLICATIONS

XP–00081613, Churchill et al., The Importance of Calcium–Related Effects on Energetics at Hypothermia: Effects of Membrane–Channel Antagonists on Energy Metabolism of Rat Liver, Cryobiology, vol. 32, ppl. 477–486 (1995).
XP–002087951, Lawrence, J. N., et al., "Development of an Optimal Method for the Cryopreservation of Hepatocytes an Their Subsequent Monolayer Culture", Toxic, in Vitro, vol. 5, No. 1, pp. 39–50 (1995).

\* cited by examiner

*Primary Examiner*—David M. Naff
*Assistant Examiner*—Deborah K. Ware
(74) *Attorney, Agent, or Firm*—Sidley Austin Brown & Wood LLP

(57) ABSTRACT

Disclosed is a universally-adaptable cell preconditioning and storage medium that can be used for the effective cryopreservation of cells at temperatures less than 4° C. The aqueous medium contains adenosine, a calcium channel blocker, and a nutrient-rich matrix that has a sufficient amount of cell metabolites to sustain the metabolic needs of the harvested cells while incubating the cells for a period of at least 10 minutes, without producing detectable levels of lactate or substantially depleting the metabolic substrates of the cell.

26 Claims, No Drawings

CELL PRECONDITIONING AND CRYOPRESEVATION MEDIUM

BACKGROUND OF THE INVENTION

1. Field of the Invention

This invention is related generally to the preservation of viable cells and in particular to a medium for conditioning and long term storage of viable cells.

2. Discussion of the Related Art

The preservation of viable cells which have been harvested from a donor source is of great importance and utility in the scientific and medical communities. Indeed, cells which have been harvested and preserved are routinely used in scientific research and development. For instance, preserved cells are often tested to aid in the development of medical treatments or to provide information on physical or chemical properties of the cells. Further, a collection of readily available viable cells allows scientists to conduct experiments at times which are suitable to laboratory availability or the researcher's schedule. To be useful, the preserved cells must retain the integrity and viability of the cells at the time of harvest. Thus, the process of preserving the cells must not, in itself, damage or destroy the cells.

In conventional cryopreservation techniques, cells are harvested, suspended in a storage solution, then preserved by freezing. When the cells are to be used, they are thawed, for example, cells taken from human donor sources are brought back to the normal human body temperature (i.e., approximately 37° C.), and then placed in a cell culture medium. Cryopreservation protocols subject the cells to a multitude of stresses and insults throughout the process of cell harvesting, freezing, and thawing. These stresses and insults can cause irreparable damage to the cell.

Ischemia, a lack of blood flow, occurs as soon as the life of the cell's donor is terminated. Immediately thereafter, the cell experiences hypoxia, or oxygen deprivation, due to the lack of blood flow. Hypoxia causes anaerobic metabolism in normally aerobic cells. Anaerobic metabolism produces toxic byproducts, such as the build-up of lactic acid (acidosis). Some of the byproducts of anaerobic metabolism produce oxygen free-radicals that damage or destroy the cells when the cells are reoxygenated. Accordingly, prior to taking a tissue sample, the temperature of the donor source is reduced such that metabolic activity in the cells of the donor source is minimized. Reduction of temperature of the donor source reduces the energy state of the cells which aids in reducing the affects of ischemia and hypoxia. Typically, the temperature of the donor source is lowered to 4° C. Although some residual metabolic activity exists in the cells at 4° C., 4° C. is about the lowest temperature available which does not cause the formation of ice crystals on the cells.

The cells are typically isolated from the tissue sample by addition of a hydrolytic enzyme. The hydrolytic enzyme deteriorates the extracellular tissue structure, thus causing the release of the desired cells. Unfortunately, the hydrolytic enzyme also harms the isolated cells. Some of the cells are destroyed during isolation. Other cells are weakened by exposure to the hydrolytic enzyme. It is believed that cells weakened by such enzymatic insult are less viable.

Once the cells are harvested, the cells are suspended in a storage solution which is also, typically, at 4° C. One example of a widely used cell storage medium is Dulbecco's Modified Eagle Medium ("DMEM"), an aqueous solution containing 10 wt. % fetal calf serum and low levels of glucose. DMEM is intended to provide support for the minimal metabolic activity which occurs just before the cells are frozen and just after the cells are brought to normal body temperature. Because cells are frozen as soon after harvest as possible, in order to completely arrest cell metabolism, the amount of glucose needed to support metabolic activity is quite low.

The harvested cells can also be harmed by the initial freezing and the subsequent thawing of the cell suspension. The cell membranes can be damaged primarily due to the rapid change in osmotic pressure that results when liquid inside or outside the cell is frozen or thawed. Freezing and thawing of the cell suspension causes a dramatic change in the concentration of liquid on one side of the membrane relative to the other. The dramatic change in concentration creates an osmotic pressure differential. The transmembrane pressure differential causes liquid to flow into the cell or liquid in the cell to flow out of the cell to reach equilibrium osmotic pressure. When excess liquid flows into a cell, the cells burst. When too much liquid leaves a cell, the cell shrivels and dies.

It is known to add cryopreservatives to a cell storage medium, such as DMEM, to prevent cell damage during freezing. Cryopreservatives include dimethyl sulfoxide (DMSO), glycerol, propylene glycol, and other large molecules with a high bonding affinity to water. Cryopreservatives are absorbed into the cells and have sufficient size that they are not likely to be rapidly transported across the membrane. Thus, when osmotic pressures change, the water remains bound to the cryopreservative and is stabilized to the change in transmembrane osmotic pressure. Of all the cryopreservatives, DMSO is by far the most preferred because of its high bonding affinity to water. However, DMSO is toxic to cells if added when the cells are at normal body temperature, and it is generally rapidly added to the cells just before the cells are frozen, i.e., when the temperature of the cells has been lowered to approximately 4° C. Furthermore, the cells must be carefully washed to remove DMSO after the cells are subsequently thawed to a temperature of about 4° C.

In addition to the above-stated problems, current preservation protocols are limited in that they are not necessarily transferrable between samples. Indeed, the type of sample has, in part, dictated the requirements of the preservation technique such that the technique employed is dependent, in part, upon the sample to be stored. Examples of various techniques of freezing and thawing of different sample types are found, for example, in U.S. Pat. No. 4,004,975 to Lionetti et al., directed to freezing and thawing of human white cells; U.S. Pat. No. 4,890,457 to McNally et al., directed to the freezing and thawing of collagen-rich tissue, such as heart valves; and U.S. Pat. No. 4,965,185 to Grischenko et al., directed to the freezing and thawing of embryos, more specifically, mammal embryos.

U.S. Pat. No. 5,328,821 to Fischer et al. discloses a cryopreservation solution for tissue slices. The solution contains (a) glucose and (b) a cryopreservative. Other ingredients include (c) impermeates, such as potassium gluconate, potassium saccharate, and mannitol, to prevent or minimize hypothermic induced cell swelling, (d) hydrogen ion buffers, such as a phosphate, (e) adenosine, an ATP precursor for the regeneration of high energy phosphate compounds, (f) free-radical inhibitors, such as allopurinol and mannitol, (g) reducing agents, such as glutathione, (h) inorganic salts, such as KCl, $MgSO_4$, MgCl, $NaHCO_3$, and $KHCO_3$, (i) vitamins, such as vitamin E and vitamin C, (j)

hormones, such as dexamethasone and insulin, (k) calcium channel blockers, such as verapamil, and (l) acid generating substrates, such as succinate, fructose and glucose. One of the drawbacks of the cell cryopreservation solution described in the Fischer et al. patent is that its use is limited to cryopreservation of tissue slices. Consequently, the utility of the solution disclosed in the Fischer patent has unproven effectiveness with harvested cells that have been weakened because they have been isolated by treatment with a hydrolytic enzyme.

Although some cryopreservation protocols have altered the conventional methods, these altered methods have failed to address all of the above mentioned problems. For instance, U.S. Pat. Nos. 5,171,660 and 5,424,207, both to Carpenter et al., describe an alternative to the immediate freezing of tissue samples. These patents give examples of placing heart leaflets in DMEM and then preincubating the tissue, for from about 5 minutes to about 24 hours, at a temperature of from about 27° C. to about 42° C. The preincubation is said to assure that the metabolic energy status and functional capacity of the tissue are restored when the tissue is thawed.

In U.S. Pat. No. 4,559,298 to Fahy, directed to vitrification of biological material, the cryopreservative is introduced and removed in step-wise concentrations. Specifically, the method in Fahy uses step-wise concentrations of greater than 10% per step. The large step-wise additions are aimed at inhibiting re-establishment of the isotonic volume of the cells prior to vitrification, i.e., osmotic equilibrium of the cells is not desired. Further, despite the step-wise addition and removal of a cryopreservative, intra-cellular concentrations are about 30% which is too high of a concentration and is not acceptable for some sample types, such as, for example, eukaryotes and aerobic prokaryotes. In U.S. Pat. No. 4,890,457 to McNally et al., which is directed toward collagen-rich tissue, the cryopreservative, DMSO, is removed in a 2.5% step-wise concentration. Nonetheless, the cryopreservative is not introduced in the same gradual step-wise concentrations, thus, potentially introducing cell stresses prior to freezing.

Thus, there remains a need for a generally applicable method for cell cryopreservation that more effectively maintains the integrity, viability and function of all types of cells during the cryopreservation process, more specifically, eukaryote, and aerobic prokaryote cells. The present invention satisfies these and other needs and provides further related advantages.

SUMMARY OF THE INVENTION

The present invention is a universally-adaptable cell preconditioning and storage medium that can be used for the effective cryopreservation of cells at temperatures less than 4° C. The aqueous medium contains adenosine, a calcium channel blocker, and a nutrient-rich matrix that has a sufficient amount of cell metabolites to sustain the metabolic needs of the harvested cells while incubating the cells, generally at a temperature of from about 35° C. to about 38° C., preferably, about 37° C. for a period of at least 10 minutes, preferably about 25 minutes, without producing detectable levels of lactate or substantially depleting the metabolic substrates of the cell.

Adenosine is included in the cell medium, typically in a concentration ranging from about 2.7 mM to about 3.6 mM. Preferably, the adenosine concentration ranges from about 2.9 mM to about 3.1 mM, and, more preferably, is about 3.0 mM. The adenosine is rapidly converted by the cells into adenosine triphosphate to supply immediate energy to the cells during preconditioning. The medium can also include other cell energy sources, such as saccharides like glucose, or metabolites of glucose, such as pyruvate.

A calcium channel blocker is included in the cell medium to prevent calcium-regulated membrane transport of the adenosine. An example of a preferred calcium channel blocker is verapamil. In one embodiment, verapamil is added to the cell medium in an amount ranging from about 0.04 mM to about 0.07 mM. It is added preferably in an amount ranging from about 0.05 mM to about 0.06 and more preferably in an amount of about 0.05 mM.

The other cell metabolites include nutrients that are easily absorbed into the cells to be preserved. Representative nutrients include one or more amino acids selected from alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. Additionally, the cell metabolites. preferably include one or more vitamins selected from the group comprising pantothenate, choline chloride, folic acid, inositol, niacinamide, pyridoxal, riboflavin, and thiamine. The concentration of the amino acids is chosen to match the amino acid concentration found in the healthy cytoplasm of the cells to be preconditioned. Alternatively, the concentration of amino acids in the medium is chosen to be proportional to the metabolic needs of the cells during normal cell metabolism.

In some embodiments, the cell medium includes an inorganic salt. Suitable salt-forming inorganic anions include chloride, phosphate, sulfate, and selenite. Suitable salt-forming inorganic cations include sodium, potassium, magnesium, copper, and zinc cations. And in some embodiments, the cell medium has a concentration of inorganic salts substantially equal to the concentration of inorganic salts found in the in vivo donor cells.

Also in some embodiments, the cell cryopreservation medium contains at least one hormone. Representative hormones include insulin, and preferably bovine pancreas insulin; dexamethasone; leutropic hormone and preferably sheep leutropic hormone; transferrin and preferably human transferrin; somatropin; linoleic acid; fetal bovine serum.

In some embodiments, the medium also contains a cryopreservative for protecting the cells during freezing and thawing. Preferably, the cryopreservative is DMSO.

It is also preferable for the medium to include a oxygen free radical scavenger to protect the cells from oxygen free radicals produced during reoxygenation after storage. Most preferably, the oxygen free radical scavengers are allopurinol and/or glutathione. Alternatively, the cell salvage medium comprises glycine, glutamine, glutamic acid, and cysteine, proteins that are rapidly converted by the cell into glutathione.

The cell medium preferably is buffered with a mild buffer solution having a content and concentration such that the cell medium has a first pH that ranges from about 7.3 to about 7.5 at a temperature above 35° C. and has a second pH ranging from about 6.3 to about 6.6, preferably form about 6.4 to about 6.5, and most preferably about 6.4, at a temperature below about 4° C. A suitable buffer includes a sodium carbonate buffer, an N-[Hydroxyethyl]piperazine-N' [2-ethananesulfonic acid] ("HEPES") buffer or a combination of the two. Overall, the concentration of all of the components preferably create a solution that is slightly hyperosmolar.

The present invention is also directed to a preserved cell sample, that includes a sample of eukaryotic or prokaryotic cells, suspended and frozen, preferably at the boiling point of liquid nitrogen, in the cell cryopreservation medium, as well as to a kit for preserving a sample of cells comprising a storage vessel and the cell cryopreservation and cryopreservation medium. In some embodiments, the kit further includes instructions to incubate cell at 37° C. for a period ranging from about 10 minutes to about 1 hour and preferably about 25 minutes prior to storing the cells at a temperature below 4° C. Preferably, the kit also includes an oxygen source for oxygenating the cell preconditioning and cryopreservation and medium during the preconditioning. Most preferably, the kit includes instructions to oxygenate the solution with a gas having an oxygen content of no less than 80 vol. % while the cells are incubated at 37° C.

DETAILED DESCRIPTION OF THE PREFERRED EMBODIMENTS

The present invention is a universally-adaptable, aqueous cell preconditioning and cryopreservation medium useful for preserving cells at temperatures less than 4° C. and in some embodiments less than 0° C. The same medium is used to first precondition the cells thereby effectively reinvigorating cells damaged by harvesting from a donor source. Unlike conventional cell storage media, the inventive cell medium is capable of sustaining aerobic metabolism for a period of at least 10 minutes, preferably at least about 25 minutes, without producing detectable levels of lactate or substantially depleting the metabolic substrates of the cell. After preconditioning, the same cell media is used as an effective medium for cryopreservation of the cells. Furthermore, the cell medium also can be used after storage during reconditioning and reoxygenation of the preserved cells.

The cell medium contains adenosine, typically in a concentration ranging from about 2.7 mM to about 3.6 mM. Preferably, the adenosine concentration ranges from about 2.9 mM to about 3.1 mM, and, more preferably, is about 3.0 mM. Adenosine is rapidly converted by cells into adenosine triphosphate. The adenosine triphosphate is a cell energy source immediately available to promote cell growth and regeneration during preconditioning.

The cell medium can also include other cell energy sources, such as saccharides. Any saccharide, such as glucose, or metabolite of the glycolytic pathway, such a pyruvate, a metabolite of glucose, can be added to the cell cryopreservation medium as a potential energy source. The cell medium of one embodiment contains glucose in an amount ranging from about 18 mM to about 24 mM. Preferably, the solution contains glucose in an amount ranging from about 19 mM to about 21 mM, and most preferably about 20 mM. The cell medium of another embodiment contains sodium pyruvate in an amount ranging from about 0.9 mM to about 1.1 mM, preferably, about 1.0 mM.

The cell medium also includes a calcium channel blocker to prevent the calcium-regulated export of adenosine from the cell. This allows higher levels of adenosine in the cell which fortifies the cell with rapidly available energy. An example of a suitable calcium channel blocker is verapamil. In one embodiment, verapamil is added to the cell medium in an amount ranging from about 0.04 mM to about 0.07 mM. It is added preferably in an amount ranging from about 0.05 mM to about 0.06 and more preferably in an amount of about 0.05 mM.

Importantly, the cell medium contains various cell metabolites, such as nutrients that are easily absorbed into the cells during preconditioning. For example, the cell medium preferably contains one or more amino acids. Since each of the amino acids can be absorbed by the cell and consumed during the cell's normal metabolism, it is preferable to have a concentration of all amino acids in the cell medium. However, it is believed that the addition of any amino acid will serve to strengthen the cell during preconditioning, even if other amino acids are not present.

The concentration of the amino acids is chosen to match the amino acid concentration found in the healthy cytoplasm of the cells to be preconditioned. Alternatively, the concentration of amino acids in the medium is chosen to be proportional to the metabolic needs of the cells during normal cell metabolism. Some amino acids are used more frequently and should be present in higher amounts.

L-alanine is preferably added in an amount ranging from about 0.09 mM to about 0.11 mM and more preferably added in the amount of about 0.10 mM. Arginine is preferably added in an amount ranging from 0.6 mM to about 0.8 mM and is more preferably added in an amount of about 0.7 mM. Asparagine and/or aspartic acid are preferably added in a total amount ranging from about 0.9 mM to about 1.1 mM and most preferably added in an amount of about 1.0 mM. In one embodiment, the ratio of asparagine to aspartic acid is 10:1.

Cysteine is preferably added in an amount ranging from about 0.9 mM to about 1.1 mM and most preferably added in an amount of about 1.0 mM. Glutamine and/or glutamic acid are preferably added in a total amount ranging from about 2.7 mM to about 3.3 mM and more preferably added in an amount of about 3.0 mM. The ratio of glutamine to glutamic acid is about 2:1 in one embodiment of the present invention. Glycine is preferably added in an amount ranging from about 0.9 mM to about 1.1 mM and more preferably added in an amount of about 1.0 mM. Histidine is preferably added in an amount ranging from about 0.25 mM to about 0.30 mM and more preferably added in an amount of about 0.28 mM. Isoleucine is added in an amount preferably ranging from about 0.7 mM to about 0.9 mM and more preferably added in an amount of about 0.8 mM. Leucine is added in an amount ranging from 0.7 mM to about 0.9 mM and more preferably added in an amount of about 0.8 mM.

Lysine is added in an amount ranging from about 0.7 mM to about 0.9 mM and more preferably added in an amount of about 0.8 mM. Methionine is added in an amount ranging from 0.18 mM to 0.22 mM and more preferably added in an amount of about 0.20 mM. Phenylalanine is added in an amount ranging from about 0.35 mM to 0.45 mM and more preferably added in an amount of about 0.40 mM. Proline is added in an amount ranging from about 0.09 mM to about 0.11 mM and more preferably added in an amount of about 0.10 mM. Serine is added in an amount ranging from about 0.35 mM to about 0.45 mM and more preferably added in an amount of about 0.40 mM. Threonine is added in an amount from about 0.35 mM to about 0.45 mM and more preferably added in an amount of about 0.40 mM. Tryptophan is added in an amount ranging from 0.12 mM to about 0.15 mM and more preferably added in an amount of about 0.13 mM. Tyrosine is added in amount ranging from about 0.55 mM to about 0.65 mM and more preferably added in an amount of about 0.60 mM. Valine is added from about 0.7 mM to about 0.9 mM and more preferably 0.8 mM.

Additionally, the cell media preferably contains one or more vitamins selected from the group comprising pantothenate, choline chloride, folic acid, inositol, niacinamide, pyridoxal, riboflavin, and thiamine. Vitamins are supplied to fortify the cell after cell harvesting. They serve to replenish vitamins lost during treatment with the hydrolytic enzyme or that might have been deficient in the donor source of the cells.

While it is preferred that all of the known vitamins are added to the cell medium. the addition of vitamins are optional. In one embodiment, the following vitamins are added in the stated amounts. Pantothenate is added in an amount ranging from about 0.003 to about 0.009 mM and more preferably about 0.008 mM. Choline chloride is preferably added in an amount ranging from about 0.026 mM to 0.032 mM and more preferably about 0.029 mM. Folic acid is added in an amount ranging from about 0.008 mM to 0.010 mM and more preferably about 0.009 mM. Inositol is added in an amount ranging from about 0.036 mM to 0.044 mM and more preferably about 0.040 mM. Niacinamide is added preferably in an amount ranging from about 0.030 mM to 0.036 mM and more preferably about 0.033 mM. Pyridoxal is added in an amount ranging from about 0.018 mM to 0.022 mM and more preferably about 0.020 mM. Riboflavin is added in an amount ranging from about 0.0009 mM to 0.0011 mM and more preferably about 0.001 mM. Thiamine is added in an amount ranging from about 0.011 mM to 0.013 mM and more preferably about 0.012 mM.

In some embodiments, the cell medium contains one or more inorganic salt. The salt is added to the medium to prevent the cell reserves from being depleted. Since the inorganic ions forming the salts are very small, they readily pass through the cell membrane and are lost from the cell. Suitable inorganic anions include chloride, phosphate, sulfate, or selenite ions. Suitable inorganic cations include sodium, potassium, magnesium, copper, or zinc ions. In these embodiments, the cell medium preferably has a concentration of inorganic ions substantially equal to the intercellular concentration of the ions in a cell in vivo.

In preferred embodiments, the cell medium contains inorganic salts in an amount sufficient to create a slightly hypertonic medium, i.e., is slightly hypertonic compared to the osmolarity of the cell cytoplasm. The cells shrink slightly when in such a slightly hypertonic medium. Thus, there is less stress on the membrane which benefits the cell during cold preservation and cryopreservation. Accordingly, in a preferred embodiment, the cell medium has an osmolarity of approximately 330 mOsml/L.

The following concentration of salts have been found effective in maintaining appropriate ionic levels. Sodium chloride is added preferably in an amount ranging from 110 mM to about 120 mM and more preferably in an amount of about 115 mM. Potassium chloride is added preferably in an amount ranging from approximately 4.75 mM to 5.25 mM and more preferably in an amount of about 5 mM. Potassium phosphate is added preferably in an amount ranging from about 2.85 mM to about 3.15 mM and more preferably in an amount of about 3 mM. Magnesium sulphate is added preferably in an amount ranging from 1.15 mM to about 1.25 mM and more preferably in an amount of approximately 1.2 mM.

Copper sulfate is available in a hydrated form ($CuO_4.H_2O$) and is added in an amount ranging from approximately 8.5 mM to approximately 9.4 mM and more preferably 8.9 mM. Zinc sulphate is available in a hydrated form having a formula ($ZnSO_4.H_2O$) and is added in an amount ranging from $4.2 \times 10^{-8}$ mM to about $4.6 \times 10^{-8}$ mM and more preferably $4.4 \times 10^{-8}$ mM. Sodium selenite ($Na_2SeO_3$) is preferably added in an amount ranging from about $2.8 \times 10^{-6}$ through $3.2 \times 10^{-6}$ mM and more preferably $3.0 \times 10^{-6}$ mM.

Also in some embodiments, the cell cryopreservation medium contains at least one hormone. Suitable hormones include insulin, and preferably bovine pancreas insulin; dexamethasone; leutropic hormone and preferably sheep leutropic hormone; transferrin and preferably human transferrin; somatropin; linoleic acid; and fetal bovine serum.

Because the cell suspension is to be frozen, a cryopreservative is preferably added to the cell medium. Suitable cryopreservatives include DMSO, glycerol, propylene glycol, and other large molecules with a high bonding affinity to water, with DMSO being most preferred. Since DMSO is potentially toxic, it is not added to the cell medium until after the cell medium has been combined with the cells and the resulting suspension cooled to a temperature below that which DMSO adversely affects the cells. It is preferred that DMSO be added to the suspension at a temperature at or below about 4° C. In one embodiment of the invention, the DMSO has a concentration ranging from about 8 vol. % to about 15 vol %. Preferably, the concentration of DMSO is about 12 vol. %.

It is also preferable for the cell medium to include an oxygen free-radical scavenger to protect the cells from any oxygen free-radicals that may be present during reoxygenation after storage. Oxygen free-radicals are highly reactive and cause considerable damage to a cell. Typically, oxygen free-radical scavengers are large organometallic molecules that readily react with the oxygen free-radicals, before the radicals can damage the cell.

Preferred oxygen free-radical scavengers include allopurinol and/or glutathione. In one embodiment, allopurinol is added in an amount ranging from about 0.9 mM to about 1.2 mM and is added more preferably in an amount of about 1 mM. In another embodiment, glutathione is added in an amount ranging from about 2.7 mM to about 3.6 mM. It is added preferably in an amount ranging from about 2.9 mM to about 3.1 mM and is added more preferably in an amount of about 3.0 mM.

Alternatively, the cell produces glutathione naturally when glutathione levels are low. Glutathione is formed from three amino acids, namely glycine, glutamate, and cysteine. Thus, the oxygen free radical scavenger function can be satisfied or, at least, supported by a medium that combines these three amino acids.

The cell medium of one embodiment is buffered. The normal pH of a cell is typically about 7.4 but can fluctuate under normal situations. In a healthy cell in vivo the pH will fall within a first range of from about 7.3 to about 7.5 without dramatically affecting the performance of the cell. During cell cooling, the pH of the cell becomes more acidic. As the cell becomes acidic, the enzymes of the cell do not function normally which arrests the cell metabolism and other enzymatic activity.

Conventional cell cryopreservation media are buffered so as to maintain the pH of the medium at the pH of natural extracellular fluid during the entire preconditioning and cryopreservation process. In contrast to such conventional media, in some embodiments, the buffer included with the inventive cell medium allows the pH of the medium to drop from about 6.3 to about 6.6, preferably form about 6.4 to about 6.5, and most preferably about 6.4, when the cell suspension is cooled to temperature of about 4° C.

Preferred buffers include a sodium carbonate buffer, an N-[Hydroxyethyl]piperazine-N'[2-ethananesulfonic acid]

("HEPES") buffer or a combination of the two. In accordance with a most preferred embodiment, the amount of sodium bicarbonate ranges from about 22.5 mM to about 27.5 mM, preferably from about 24 mM to about 26 mM and, more preferably, about 25 mM, while the amount of HEPES ranges from about 9 mM to about 11 mM and more preferably about 10 mM.

When, the cell medium is combined with the cell samples at 37° C., the pH of the mixture should be within the above stated first range of from about 7.3 to about 7.5 and should preferably be as close to 7.4 as possible. Then, as the sample is cooled, the pH will drop. When the pH is 4° C., the pH should fall within the above stated second range of from about 6.3 to about 6.6, preferably form about 6.4 to about 6.5, and most preferably about 6.4. If the pH does not fall within the second range or it is desired that the medium have a pH closer to 6.4, the medium can be titrated with a mild sodium carbonate solution or a mild carbonic acid solution to adjust the pH to the desired value. One benefit of the inventive medium is that the pH will return to a pH close to 7.4 when the cells are warmed to 37° C.

The method of using the cell medium is described in copending application by the inventors of the present patent application and which is filed the same day as the present application. This application is Ser. No. 09/168,366, now U.S. Pat. No. 6,140,123 and is fully incorporated by reference into the present application.

The method begins by taking harvested eukaryotic or prokaryotic cells and suspending the cells in the cell medium, while maintaining the temperature at about 35–40° C., and more preferably about 37° C. The medium is oxygenated by bubbling oxygen through the solution using a gas having an oxygen content of no less than 80 vol. %. In one embodiment, the medium is saturated at a pressure exceeding atmospheric pressure. The cells are preconditioned in this matter for a period ranging from about 10 minutes to about 48 hours. Preferably, the cells are preconditioned for a period ranging from about 10 minutes to about 2 hours, and more preferably about 25 minutes.

The cell suspension is then cooled to about 4° C. DMSO is slowly added to the suspension until the amount of DMSO reached has a concentration ranging from about 8 vol. % to about 15 vol %., preferably about 12 vol. %. The suspension is placed in cryo-vials for freezing. Cryo-vials containing the suspension are first placed in a freezer that maintained at −70° C. for about two hours to allow the water inside the cell to penetrate into extracellular space. Then the cryo-vials are transferred to the vapor phase of a liquid nitrogen tank for 10–24 hours. Thereafter, the cryo-vials are immersed in liquid nitrogen for long term storage at −196°, the boiling point of liquid nitrogen.

The cells are recovered by placing the frozen suspension in a water bath maintained at 37° C.–42° C. and gently agitating until the temperature of the cell suspension reaches 37° C. The cell suspension is then transferred into a round bottom glass tube, spun to separate the cells from a supernatant, and the supernatant removed. Next the cells are washed with additional cell cryopreservation medium, including DMSO, and having an osmolarity of 1500 mOsml/l . The cell medium is slowly added to the cells and the cells resuspended. After resuspension, the cells are spun the supernatant again removed, and the cells recovered. The cells are then washed with an oxygenated cell cryopreservation medium that includes DMSO but has an osmolarity of 900 mOsml/l. Finally, the cells are resuspended in a cell cryopreservation medium having no DMSO, spun, and recovered. The cells are then ready for use.

The present invention also comprises a kit for storage of cells. The kit includes a cell medium as described above with a vessel for containing the cells. Also included in the kit is a set of instructions. The instructions include directions on using the cell medium in accordance with the principles of the present invention. In one embodiment, the instructions direct the user to oxygenate the cell medium and precondition the cells at a temperature of approximately 37° C. for a length of time ranging from about 10 minutes to about 48 hours. According to this embodiment, the kit preferably includes a source of oxygen and an oxygen delivery device. The oxygen delivery device enables the medium to be saturated with oxygen.

The instructions according to another embodiment of the invention, provide directions to measure the pH of the medium when the medium is at a temperature of about 4° C. The directions further include instructions on titrating the medium to a pH of about 6.3 to about 6.5, preferably about 6.4.

The present invention also includes a preserved cell sample that includes a sample of eukaryotic or prokaryotic cells suspended in a cell medium according to the principles of the present invention. The cell sample is preferably kept at a temperature below 4° C. In another embodiment the cell sample is frozen and is preferably frozen at the boiling point of liquid nitrogen.

The following examples are included to further illustrate the invention. They are not limitations thereon.

EXAMPLES

Example 1

DMEM Control

Porcine hepatocyte cells were harvested at 37° C. and placed into eight cryo-vials. The temperature of the eight vials was reduced to 4° C. Each vial was divided into two aliquots of $1.8 \times 10^7$ cells in 0.9 ml distilled, deionized water and each aliquot placed in a separate vial. The aliquots were then spun at 600 rpm for 1 minute and the supernatant removed. The resulting cell pellets were resuspended in 1.8 ml DMEM with 10% DMSO under gentle agitation. A cell sample was obtained for viability/morphology testing. The remainder of each cell suspension was transferred into a 2 ml cryo-vial and each cryo-vial was then sealed.

The 2 ml cryo-vials were then transferred to a −70° C. freezer. After two hours, the cryo-vials were transferred to the vapor phase of a liquid nitrogen tank and held for 10–24 hours. Then, the vials were immersed into the liquid phase of the nitrogen tank and stored for 20 days.

After freezing, the cell suspensions were restored by submerging in a 37–42° C. water bath and agitating until each cell suspension was thawed. A second cell sample was obtained for viability/morphology testing. The remainder of each cell suspension was transferred into a separate round bottom glass tube and 3.6 ml of DMEM was added to each suspension under constant gentle agitation. The cell suspensions were then spun at approximately 600 rpm for 1 minute. The resulting supernatant was removed and the cell pellets were resuspended in 1.5 ml of DMEM. Another sample was obtained for viability/morphology testing. The cell suspensions were each then transferred to a small petri dish (35 ml in diameter) and incubated at 37° C. for sixty minutes. A fourth sample was obtained for viability/morphology testing.

Cell viability was tested using a standardized trypan blue exclusion procedure. Morphology was tested by using light microscopic evaluation. A scoring system from 1–4 for blebbing of viable cells was used. A score of 1 represented almost no blebs. A score of two represented minor blebbing (approximately 25%). A score of 3 represented moderate blebbing (approximately 50%). A score of 4 represents severe blebbing (greater than 75% blebs). The results are reported in Table 2.

Example 2
Cell Medium with a Single Addition of DMSO at Warm Temperatures (CM Single Warm)

Porcine hepatocyte cells were harvested at 37° C. and placed into eight cryo-vials. Each vial was divided into two aliquots of $1.8 \times 10^7$ cells in 0.9 ml distilled, deionized water and each aliquot placed in a separate vial. The temperature of each aliquot was maintained at approximately 37° C. The aliquots were then spun at 600 rpm for 1 minute and the supernatant removed. The resulting cell pellets were resuspended in 2.7 ml of an oxygenated cell medium in accordance with the invention having the composition shown in Table 1.

TABLE 1

Cell Conditioning and Cryopreservation Medium

| | |
|---|---|
| Sodium Chloride | 115.00 mM |
| Potassium Chloride | 5.00 mM |
| Potassium Phosphate | 3.00 mM |
| Magnesium Sulfate | 1.20 mM |
| Copper Sulfate | $8.90 \times 10^{-8}$ M |
| Zinc Sulfate | $4.38 \times 10^{-11}$ M |
| Sodium Selenite | $3.00 \times 10^{-9}$ M |
| Sodium Bicarbonate | 2500 mM |
| N-[Hydroxyethyl]piperazine-N'-[2-ethananesulfonic acid] | 10.00 mM |
| L-Alanine | 0.10 mM |
| L-Arginine-HCl | 0.73 mM |
| L-Asparagine | 0.10 mM |
| L-Aspartic Acid | 1.00 mM |
| L-Cysteine | 1.00 mM |
| L-Glutamine | 2.00 mM |
| L-Glutamic Acid | 1.00 mM |
| Glycine | 1.00 mM |
| L-Histidine HCl.H$_2$O | 0.28 mM |
| L-Isoleucine | 0.80 mM |
| L-Leucine | 0.80 mM |
| L-Lycine.HCl | 0.80 mM |
| L-Methionine | 0.20 mM |
| L-Phenylalanine | 0.40 mM |
| L-Proline | 0.10 mM |
| L-Serine | 0.40 mM |
| L-Threonine | 0.40 mM |
| L-Tryptophan | 0.13 mM |
| L-Tyrosine | 0.60 mM |
| L-Valine | 0.80 mM |
| d-Calcium Pantothenate | 0.008 mM |
| Choline Chloride | 0.029 mM |
| Folic Acid | 0.009 mM |
| i-Inositol | 0.040 mM |
| Niacinamide | 0.033 mM |
| Pyridoxal.HCl | 0.020 mM |
| Riboflavin | 0.001 mM |
| Thiamine.HCl | 0.012 mM |
| Adenosine | 3.00 mM |
| d-Glucose | 20.00 mM |
| Sodium Pyruvate | 1.00 mM |
| Insulin (Bovine Pancreas) | 273 µ/L |
| Allopurinol | 1.00 mM |
| Glutathione | 3.00 mM |
| Verapamil | 0.051 mM |
| Dexamethasone | 0.00617 mM |
| Leutropic Hormone (Sheep) | 20 µ/L |
| Transferrin (Human) | $1.28 \times 10^{-7}$ M |
| Somatropin | 10 mµ/L |
| Linoleic Acid | 34 mM |
| Fetal Bovine Serum | 10 wt. % |

The samples were transferred into small petri dishes (60 ml diameter) and each sample incubated for twenty-five minutes at 37° C. The samples were then chilled on ice to 4° C. The samples were then transferred into two round bottomed tubes and spun at approximately 600 rpms for 1 minute. The supernatant was removed from each flask.

The cell pellets resuspended in an additional 2.7 ml of the cell medium described in Table 1. Then, under gentle agitation, 0.9 ml of oxygenated cell medium as described in Table 1, along with 20% [?] DMSO was slowly added into each tube. A cell sample was obtained for viability/morphology testing.

The samples were transferred into 2 ml cryo-vials and sealed. The 2 ml cryo-vials were then transferred to a −70° C. freezer. After two hours, the cryo-vials were transferred to the vapor phase of a liquid nitrogen tank and held for 10–24 hours. Then, the vials were immersed into the liquid phase of the nitrogen tank and stored for 20 days. The frozen cell suspensions were restored by submerging in a 37° C. to a 42° C. water bath and agitating until the cell suspensions reached 37° C. A cell sample was obtained for viability/morphology testing.

Then, the cell suspensions were transferred into round bottom glass tubes and 3.6 ml of oxygenated cell medium described in Table 1 together with DMSO having a concentration of 1500 mOsmol/l, slowly added to each suspension under constant gentle agitation. The cell suspensions were spun at approximately 600 rpms for 1 minute. The supernatant was removed and the resulting cell pellets washed in 5 ml of oxygenated cell medium described in Table 1 along with DMSO having a concentration of 900 mOsmol/l. The cell suspensions were again spun at approximately 600 rpm for 1 minute, the supernatant removed, and the cell pellets resuspended in 1.5 ml of oxygenated cell medium described in Table 1. A sample was obtained for viability/morphology testing.

The cell suspensions were transferred into a 35 ml diameter petri dish and incubated at 37° C. for 60 minutes. Samples were again obtained for viability/morphology testings Cell viability/morphology tests were performed as described Example 1. The results are reported in Table 2.

Example 3
Cell Medium Multiple Additions of DMSO at Warm Temperatures (CM Multiple Warm)

Porcine hepatocyte cells were harvested at 37° C. and placed into eight cryo-vials. Each of the eight vials were divided into two aliquots. Each aliquot included $1.8 \times 10^7$ cells in 0.9 ml distilled, deionized water. The temperature of each aliquot was maintained at approximately 37° C. The aliquots were spun at 600 rpm for 1 minute and the supernatant was removed. The samples were resuspended in 2.7 ml of oxygenated cell cryopreservation medium in accordance with the invention having the composition shown in Table 1.

The cell suspensions were transferred into small petri dishes (60 ml diameter). The samples were incubated for twenty-five minutes at 37° C. The samples were then chilled on ice to 4° C. The cell suspensions were transferred into two round bottom tubes and 3.6 ml of cold oxygenated cell medium as described in Table 1, along with 900 mOsmol/l DMSO. The cell suspensions were spun at approximately 600 rpms for 1 minute. A 6.2 ml fraction of the supernatant was removed from each tube and the cell pellet resuspended in the remaining supernatant. At this point the cell concentration was $2 \times 10^7$ cells/ml.

Under gentle agitation, 5.0 ml of cold oxygenated cell medium as described in Table 1 additionally containing 1500 mOsmol/l DMSO was slowly added to each tube. The cell suspensions were spun at approximately 600 rpms for 1 minute. A 5.1 ml fraction of supernatant was removed from each tube and the cell pellets resuspended in the remaining supernatant (cell concentration $2\times10^7$ cells/ml). Under gentle agitation, 0.9 ml of oxygenated cold cell medium as described in Table 1 with 13.7 wt. % DMSO was slowly added into each tube (cell concentration $1\times10^7$ cells per ml). A cell sample was obtained for viability/morphology evaluation.

The cell suspensions were then transferred into 2 ml cryo-vials and sealed. The cryo-vials were then transferred into a −70° C. freezer. After two hours, cryo-vials were transferred into the vapor phrase of a liquid nitrogen tank for 10 to 24 hours. The cell suspensions were then immersed in liquid nitrogen and stored for 20 days.

The frozen cell suspensions were restored by submerging in a 37° C. to 40° C. water bath and agitating until the cell suspensions (cell concentration $1.8\times10^7$ cells in 1.8 ml) reached 37° C. A cell sample was obtained for viability/morphology testing. Then, the cell suspensions were transferred into round bottom glass tubes and 3.6 ml of oxygenated cell medium as described in Table 1 also containing 1500 mOsml/l DMSO slowly added to each suspension under constant gentle agitation. The cell suspensions were spun at approximately 600 rpms for 1 minute. The supernatant was removed and the cell pellets washed with 5 ml of oxygenated cell medium as described in Table 1 also containing 900 mMOsml/l. The cell suspensions were spun at approximately 600 rpms for 1 minute, the supernatant removed, and the cell pellets resuspended in 1.5 ml of oxygenated cell medium as described in Table 1, with no DMSO. A sample was obtained for viability/morphology testing.

Then, the samples were transferred into small petri dishes and incubated at 37° C. for 60 minutes. After 60 minutes, another sample was obtained for viability/morphology testing.

The samples were obtained for cell viability/morphology testing according to the procedures described in Example 1. The results are listed on Table 2.

TABLE 2

CELL VIABILITY OF CELLS CRYOPRESERVED FOR 20 DAYS

| METHOD | Viability Before Freezing | Viability After Thawing | Viability After Washing | Viability After Incubation |
|---|---|---|---|---|
| DMEM CONTROL EXAMPLE 1 | 75% | 66% | 72% | 46% |
| CPM SINGLE WARM EXAMPLE 2 | 83% | 81% | 83% | 74% |
| CPM MULTIPLE WARM EXAMPLE 3 | 92% | 86% | 84% | 77% |

Example 4

The procedure described for Examples 1–3 was repeated except that the cells were stored for a period of 7 days in liquid nitrogen. The results are reported on table No. 3.

TABLE 3

CELL VIABILITY OF CELLS CRYOPRESERVED FOR 7 DAYS

| METHOD | Viability Before Freezing | Viability After Thawing | Viability After Washing | Viability After Incubation |
|---|---|---|---|---|
| DMEM | 79% | 64% | 71% | — |
| CPM SINGLE WARM | 85% | 78% | 82% | — |
| CPM MULTIPLE WARM | 94% | 86% | 86% | — |

Example 5

The procedure described for Examples 1—3 was repeated, except that the cells were stored for a period of 27 days in liquid nitrogen. The results are repeated on Table No. 4.

TABLE 4

CELL VIABILITY OF CELLS CRYOPRESERVED FOR 27 DAYS

| METHOD | Viability Before Freezing | Viability After Thawing | Viability After Washing | Viability After Incubation |
|---|---|---|---|---|
| DMEM | 71% | 63% | 69% | 60% |
| CPM SINGLE WARM | 84% | 71% | 77% | 77% |
| CPM MULTIPLE WARM | 92% | 89% | 87% | 81% |

Example 6

The procedure described for Examples 1–3 was repeated except that the cells were stored for a period of 23 days in liquid nitrogen. The results are repeated on Table No. 5.

TABLE 5

CELL VIABILITY OF CELLS CRYOPRESERVED FOR 23 DAYS

| METHOD | Viability Before Freezing | Viability After Thawing | Viability After Washing | Viability After Incubation |
|---|---|---|---|---|
| DMEM | 74% | 64% | 72% | 58% |
| CPM MULTIPLE WARM | 85% | 82% | 84% | 78% |
| CPM MULTIPLE WARM | 92% | 92% | 89% | 79% |

Example 7

The procedure described for Example 1–3 was repeated except that the cells were stored for a period of 28 days in liquid nitrogen. The results are repeated on Table No. 6.

TABLE 6

CELL VIABILITY OF CELLS CRYOPRESERVED FOR 28 DAYS

| METHOD | Viability Before Freezing | Viability After Thawing | Viability After Washing | Viability After Incubation |
|---|---|---|---|---|
| DMEM | 75% | 66% | 72% | 46% |
| CPM RAPID WARM | 83% | 81% | 83% | 74% |
| CPM TITRATED WARM | 92% | 86% | 84% | 77% |

While the invention has been described in connection with its preferred embodiments, it will be understood that it is not intended to limit this invention thereto, but it is intended to cover all modifications and alternative embodiments falling within the spirit and scope of the invention as expressed in the appended claims.

That which is claimed is:

1. An aqueous medium for preconditioning and cryopreservation of cells harvested from a donor comprising:
   water;
   adenosine;
   a calcium channel blocker; and
   a cell nutrient matrix comprising a sufficient amount of nutrients to sustain the metabolic needs of harvested cells during an incubation period of at least 10 minutes without producing detectable levels of lactate or substantially depleting the nutrients so as to maintain viability of the harvested cells, wherein the cell nutrient matrix contains a carbon and energy source; at least one vitamin selected from the group consisting of pantothenate, choline chloride, folic acid, inositol, niacinamide, pyridoxal, riboflavin and thiamine; and at least one amino acid selected from the group consisting of alanine, arginine, asparagine, aspartic acid, cysteine, glutamine, glycine, histidine, isoleucine, leucine, lysine, methionine, phenylalanine, proline, serine, threonine, tryptophan, tyrosine and valine.

2. A cell culture suspension comprising:
   eukaryotic or aerobic prokaryotic cells suspended in an aqueous medium containing:
   adenosine,
   a calcium channel blocker; and
   a cell nutrient matrix comprising a sufficient amount of nutrients to sustain the metabolic needs of the cells during an incubation period of at least 10 minutes without producing detectable levels of lactate or substantially depleting the nutrients so as to maintain viability of the cells, wherein the cell nutrient matrix contains a carbon and energy source, at least one vitamin selected from the group consisting of pantothenate, choline chloride, folic acid, inositol, niacinamide, pyridoxal, riboflavin and thiamine; and at least one amino acid selected from the group consisting of alanine, arginine, asparagine, aspartic acid, cysteine, glutamine, glycine, histidine, isoleucine, leucine, lysine, methionine, phenylalanine, proline, serine, threonine, tryptophan, tyrosine and valine.

3. An aqueous medium for preconditioning and cryopreservation of cells harvested from a donor comprising:
   water;
   adenosine;
   a calcium channel blocker; and
   a cell nutrient matrix comprising a sufficient amount of nutrients to sustain the metabolic needs of the harvested cells during an incubation period of at least 10 minutes without producing detectable levels of lactate or substantially depleting the nutrients so as to maintain viability of the harvested cells, wherein the cell nutrient matrix contains 18–24 mM glucose; at least one vitamin selected from the group consisting of pantothenate, choline chloride, folic acid, inositol, niacinamide, pyridoxal, riboflavin and thiamine; and at least one amino acid selected from the group consisting of alanine, arginine, asparagine, aspartic acid, cysteine, glutamine, glycine, histidine, isoleucine, leucine, lysine, methionine, phenylalanine, proline, serine, threonine, tryptophan, tyrosine and valine.

4. A cell suspension comprising:
   eukaryotic or aerobic prokaryotic cells suspended in an aqueous medium containing:
   adenosine;
   a calcium channel blocker; and
   a cell nutrient matrix comprising a sufficient amount of nutrients to sustain the metabolic needs of the cells during an incubation period of at least 10 minutes without producing detectable levels of lactate or substantially depleting the nutrients so as to maintain viability of the cells, wherein the cell nutrient matrix contains 18–24 mM glucose, at least one vitamin selected from the group consisting of pantothenate, choline chloride, folic acid, inositol, niacinamide, pyridoxal, riboflavin and thiamine, and at least one amino acid selected from the group consisting of alanine, arginine, asparagine, aspartic acid, cysteine, glutamine, glycine, histidine, isoleucine, leucine, lysine, metonine, phenylalanine, proline, serine, threonine, tryptophan, tyrosine and valine.

5. An aqueous medium for preconditioning and cryopreservation of cells harvested from a donor comprising:
   water;
   from about 2.7 mM to about 3.6 mM adenosine;
   from about 0.04 mM to about 0.07 mM verapamil;
   a cryoprotectant; and
   a cell nutrient matrix comprising a sufficient amount of nutrients to sustain the metabolic needs of harvested cells when the harvested cells are maintained in oxygenated aqueous medium at a temperature of from about 35° to about 40° C. for a period of from about ten minutes to about 2 hours without producing detectable levels of lactate or substantially depleting the nutrients so as to maintain the viability of the harvested cells, wherein the cell nutrient matrix contains an energy source and at least one vitamin selected from the group consisting of pantothenate, choline chloride, folic acid, inositol, niacinamide, pyridoxal, riboflavin, and thiamine.

6. The aqueous medium for preconditioning and cryopreservation of cells harvested from a donor according to claim 5, wherein the concentration of adenosine in the aqueous medium is from about 2.9 mM to about 3.1 mM.

7. The aqueous medium for preconditioning and cryopreservation of cells harvested from a donor according to claim 6, wherein the concentration of verapamil in the aqueous medium is from about 0.05 mM to about 0.06 mM.

8. The aqueous medium for preconditioning and cryopreservation of cells harvested from a donor according to claim 5 wherein the cell nutrient matrix contains at least one amino acid selected from the group consisting of alanine, arginine, asparagine, aspartic acid, cysteine, glutamine, glycine, histidine, isoleucine, leucine, lysine, methionine, phenylalanine, proline, serine, threonine, tryptophan, tyrosine, and valine.

9. The aqueous medium for preconditioning and cryopreservation of cells harvested from a donor according to claim 8, further comprising at least one inorganic salt in a concentration equal to the concentration of the inorganic salts in the cells.

10. The aqueous medium for preconditioning and cryopreservation of cells harvested from a donor according to claim 9, wherein the inorganic salt includes chloride, phosphate, sulfate or selenile anions and sodium, potassium, magnesium, copper or zinc cations.

11. The aqueous medium for preconditioning and cryopreservation of cells harvested from a donor according to claim 10, wherein the aqueous medium is slightly hypertonic.

12. The aqueous medium for preconditioning and cryopreservation of cells harvested from a donor according to claim 10, wherein the aqueous medium has an osmolarity of approximately 330 mOsml/L.

13. The aqueous medium for preconditioning and cryopreservation of cells harvested from a donor according to claim 10, further comprising a saccharide.

14. The aqueous medium for preconditioning and cryopreservation of cells harvested from a donor according to claim 13, wherein the saccharide is glucose.

15. The aqueous medium for preconditioning and cryopreservation of cells harvested from a donor according to claim 10, further comprising pyruvate in an amount ranging from about 0.9 mM to about 1.1 mM.

16. The aqueous medium for preconditioning and cryopreservation of cells harvested from a donor according to claim 10, further comprising a hormone.

17. The aqueous medium for preconditioning and cryopreservation of cells harvested from a donor according to claim 16, wherein the hormone is insulin, dexamethasone, leutropic hormone, transferrin, somatropin, linoleic acid, or fetal bovine serum.

18. The aqueous medium for preconditioning and cryopreservation of cells harvested from a donor according to claim 17, wherein the hormone bovine pancreas insulin, sheep leutropic hormone, or human transferrin.

19. The aqueous medium for preconditioning and cryopreservation of cells harvested from a donor according to claim 10, further comprising an oxygen free radical scavenger.

20. The cell medium for preconditioning and cryopreservation of cells harvested from a donor according to claim 19, wherein the oxygen free radical scavenger is allopurinol, glutathione or a combination of glycine, glutamate, and cysteine.

21. The aqueous medium for preconditioning and cryopreservation of cells harvested from a donor according to claim 19, wherein the aqueous medium is saturated with a gas having an oxygen content of no less than 80 volume %.

22. The aqueous medium for preconditioning and cryopreservation of cells harvested from a donor according to claim 19, wherein the cryoprotectant is dimethyl sulfoxide.

23. The aqueous medium for preconditioning and cryopreservation of cells harvested from a donor in accordance with claim 19, further comprising a mild buffer solution having a content and concentration such that the aqueous medium has a first pH that ranges from about 7.3 to about 7.5 at a temperature above 35° C. and has a second pH that ranges from about 6.4 to about 6.6 at a temperature below 4° C.

24. The aqueous medium for preconditioning and cryopreservation of cells harvested from a donor of claim 23, wherein the first pH of the aqueous medium is about 7.4.

25. The aqueous medium for preconditioning and cryopreservation of cells harvested from a donor of claim 24, wherein the second pH of the aqueous medium is about 6.5.

26. The aqueous medium for preconditioning and cryopreservation of cells harvested from a donor of claim 23, wherein the buffer comprises a sodium carbonate buffer, a HEPES buffer or a combination of the two.

* * * * *